(12) United States Patent
Bar-Shalom et al.

(10) Patent No.: US 6,535,131 B1
(45) Date of Patent: Mar. 18, 2003

(54) DEVICE AND METHOD FOR AUTOMATIC IDENTIFICATION OF SOUND PATTERNS MADE BY ANIMALS

(76) Inventors: Avshalom Bar-Shalom, 30815 Kibbutz Nachsholim, Kibbutz Nachsholim (IL); Gideon Inzler, Mishol Hagan Street 18, 30900 Zichron Ya'acov (IL)

( * ) Notice: Subject to any disclaimer, the term of this patent is extended or adjusted under 35 U.S.C. 154(b) by 0 days.

(21) Appl. No.: 09/554,318
(22) PCT Filed: Aug. 23, 1999
(86) PCT No.: PCT/IL99/00452
§ 371 (c)(1),
(2), (4) Date: Sep. 19, 2000
(87) PCT Pub. No.: WO00/13393
PCT Pub. Date: Mar. 9, 2000

(30) Foreign Application Priority Data

Aug. 26, 1998 (IL) ................................................ 125940

(51) Int. Cl.⁷ .............................................. G08B 23/00
(52) U.S. Cl. ................ 340/573.1; 340/573.2; 340/573.3; 704/273
(58) Field of Search ............... 340/573.1, 573.2, 340/573.3; 704/273; 119/51.02; 367/178

(56) References Cited

U.S. PATENT DOCUMENTS

| | | | |
|---|---|---|---|
| 4,232,686 A | * 11/1980 | Kammlade, Jr. ............ 128/775 |
| 4,707,685 A | 11/1987 | Carrier et al. .............. 340/573 |
| 4,854,328 A | * 8/1989 | Pollack ........................ 128/736 |
| 4,965,552 A | * 10/1990 | Price et al. .................. 340/566 |
| 5,144,661 A | * 9/1992 | Shamosh et al. .............. 380/9 |
| 5,225,842 A | * 7/1993 | Brown et al. ............... 342/357 |
| 5,471,993 A | * 12/1995 | Yoches et al. .............. 128/778 |
| 5,576,972 A | * 11/1996 | Harrison ..................... 364/516 |
| 5,651,070 A | 7/1997 | Blunt .......................... 381/56 |
| 5,668,780 A | 9/1997 | Hsieh ......................... 367/198 |
| 5,677,675 A | 10/1997 | Taylor et al. ............... 340/568 |
| 5,842,162 A | * 11/1998 | Fineberg .................... 704/233 |
| 5,900,818 A | * 5/1999 | Lemnell .................. 340/573.3 |
| 5,901,660 A | 5/1999 | Stein ....................... 119/51.02 |
| 5,984,875 A | * 11/1999 | Brune ........................ 600/549 |
| 6,002,427 A | * 12/1999 | Kipust ........................ 348/156 |
| 6,058,889 A | * 5/2000 | Van Curen et al. ......... 119/721 |
| 6,107,918 A | * 8/2000 | Klein et al. ................. 340/511 |
| 6,167,839 B1 | * 1/2001 | Isaksson et al. ......... 119/14.08 |

* cited by examiner

Primary Examiner—Daniel J. Wu
Assistant Examiner—Phung T Nguyen
(74) Attorney, Agent, or Firm—Abelman, Frayne & Schwab (57) ABSTRACT

An apparatus for automatically identifying when an animal is in distress receives a sound pattern produced near the selected animal and compares it with pre-stored audio patterns corresponding to respective sounds expected to be produced by that type of animal when in various types of distress to determine the best match. When a good enough match is made, a signal is automatically sent to a remote communication unit near an attendant.

23 Claims, 5 Drawing Sheets

DEVICE AND METHOD FOR AUTOMATIC IDENTIFICATION OF SOUND PATTERNS MADE BY ANIMALS

FIELD OF THE INVENTION

The present invention relates to a method and a device for automatically identifying sound patterns accompanying physiological processes and activities of an animal in general, and uttered by an animal in distress in particular, especially of a pregnant animal going into labor, for storing, analyzing and processing data related to said identified sound patterns and deviations therefrom, and for providing an attendant with respective alert signals and data, according to pre-programmed requirements.

BACKGROUND OF THE INVENTION

In general, certain physiological processes and activities of animals, e.g. cardiac, respiratory, digestive or ruminative processes and activities, are accompanied with distinctive sound patterns indicative thereof. Particularly, an animal or a group of animals while in distress, e.g. presence of a predator, fire, lack of water or food, and especially a pregnant animal going into labor, utter distinctive sound patterns indicative thereof. Automatically identifying said sound patterns and alerting an attendant to provide the required assistance, can be most advantageous.

For instance, it is widely known that many calves die during birth. In extreme cases the mother may also die during labor. It may be noted that on the average, 5%–10% of new born calves die during birth. Death of a calf, especially of livestock, is a significant money loss to the farmer, due to the relatively high price of calves. During 1997 in Israel alone, some 7,400 calves died during birth, 4,100 of which were males and 2,300 were females. A newborn calf is valued at NIS 1,100.- and the income generated by a cow during its life span is valued at NIS 25,000.-.

It is well established in the art, that the presence of an attendant assisting the mother during birth, reduces significantly the rate of mortality of the newborns. The exact time of birth cannot be predicted with any accuracy, hence, the presence of an attendant for assisting the animal during delivery cannot be ensured. Furthermore, the presence of an attendant during regular working hours, provides only a partial solution to the problem. But, as the attendant cannot be in the proximity of the pre-parturient animal during all hours of the day, in particular during the "quiet hours", i.e. late evening, night and the small hours, when most births occur, the beginning of parturition should be automatically identified and alert signal given to an attendant.

Further, distinctive sound patterns accompanying cardiac and respiratory activities and deviations therefrom, may be indicative of other distress conditions of an animal, such as heat stroke, diarrhea, swollen belly, etc. For instance, distinctive sound patterns accompanying disturbances in swallowing (dysphagia), in digestion (dyspepsia), in cardiac or respiratory activities, are indicative of a horse in distress. Also, dogs and cats while in distress, experience cardiac or respiratory changes accompanied by distinctive sound patterns. According to the present invention, all said sound patterns are identified and compared to pre-stored sound patterns, thereby alerting an attendant who may not be in proximity to an animal or a group of animals requiring urgent assistance. The same holds true for birds and fowl which utter distinctive sound patterns when in distress, such as rise in body temperature, lack of water, etc. Thus, all said distress situations should be automatically identified and alert signal given to an attendant.

Sound patterns of an animal, can be received by mounting an audio receiving device on an animal or under its skin or in proximity to an animal or a group of animals, whereby the device according to the present invention identifies sound patterns of a single animal or of a group of animals.

Furthermore, said identified distinctive sound patterns, and deviations therefrom, may be stored, analyzed and processed, thus provide valuable data of the state of an animal or a group of animals, according to pre-programmed requirements. By receiving, identifying, storing, analyzing and processing said sound patterns, an attendant is provided with data according to pre-programmed requirements, whereby he can learn about the physiological processes and activities and behavior of an animal or a group of animals. For example, in livestock, when said data shows deviation from normal digestive sound patterns, an attendant may learn about possible constipation or diarrhea in an animal. Further, when said data shows deviation from the normal of the rate of ruminative process, an attendant can learn about possible problems related to the food quality. Yet further, when said data shows above normal cardiac activity in conjunction with various other deviations from the normal of physiological activities in livestock, an attendant can discover the causes for said deviation of cardiac activity, such as rise in the surrounding temperatures or rise in body temperature indicative of a disease, etc.

Furthermore, according to the present invention, a combination of identified sound patterns related to an increase in cardiac and respiratory rate and identified distinctive sound patterns uttered by a cow going into labor, indicate an approaching delivery.

U.S. Pat. No. 4,707,685 to Carrier et al, is directed to a device for detecting the onset of parturition of a pregnant animal. The device is mounted on the animal and detects changes in physical properties which indicate that the animal is going into labor. It will be noted that this device might be activated by accident if, for example, the animal falls or passes under a low horizontal bar or wire.

U.S. Pat. No. 4,854,328 to Pollack, is directed to an animal monitoring telltale and information system which utilizes biophysical sensing device such as a temperature sensor, a blood pressure sensor, a blood flow sensor and the like. The system transmits the data received from the biophysical sensing device.

U.S. Pat. No. 5,651,070 to Blunt, is directed to a warning device programmable to be sensitive to pre-selected sound frequencies. This device is designed for individuals which are unable to hear warning signals, such as hearing impaired and people working in an environment where warning sounds are hidden by ambient noise. The device detects sounds from devices such as a door bell, a telephone unit, a smoke detector, a security system and the like, compares the frequency of the detected sound with pre-stored frequencies and informs the user.

U.S. Pat. No. 5,668,780 to Hsieh, is directed to a baby cry recognizer which detects whether a received sound signal is within a range of pre-stored frequencies.

SUMMARY OF THE PRESENT INVENTION

It is an object of the present invention to provide a novel device for automatically identifying sound patterns accompanying physiological processes and activities of an animal in general, and uttered by an animal in distress in particular, especially of a pregnant animal going into labor, for storing, analyzing and processing data related to said identified sound patterns and deviations therefrom, and for providing an attendant with respective alert signals and data according to pre-programmed requirements.

It is another object of the present invention to provide a novel method for operating the device of the invention.

It is a further object of the present invention to provide a novel method for providing an attendant with data of said identified sound patterns, and deviations therefrom, according to pre-programmed requirements.

It is yet a further object of the present invention to provide a novel method for providing an attendant with alert signals, once sound patterns of an animal in distress are identified.

In accordance with the present invention, there is thus provided a device for automatically identifying said sound patterns accompanying physiological processes and activities of an animal in general, and uttered by an animal in distress in particular, especially of a pregnant animal going into labor, for storing, analyzing and processing data related to said identified sound patterns, and providing an attendant with respective alert signals and data according to pre-programmed requirements. The device includes an audio receiving device, for receiving sound patterns, placed in proximity to an animal or a group of animals, thereby converting the received sound patterns into an audio signal, a controller, connected to the audio receiving device, a storage unit, containing pre-stored audio patterns, connected to the controller, and a communication interface, connected to the controller, for communicating with a remote communication unit located in proximity to an attendant.

The controller processes the audio signal and compares the processed audio signal with the animal pre-stored audio pattern, thereby producing a likelihood value, representing the degree of resemblance between the audio signal and the pre-stored audio pattern, and stores said likelihood value in the storage unit.

The controller provides a command to the communication interface, to inform the remote communication unit, when the likelihood value exceeds a pre-stored value.

The device can also include a user interface, connected to the controller, for receiving programming instructions from a user, thereby the controller can be pre-programmed to identify various kinds of animal sound patterns and to process, analyze and provide data according to pre-programmed requirements.

The device can further include an animal interface, connected to the controller, for maintaining an open communication line with the animal or group of animals, thereby listening to sounds and voices in proximity thereto and confirming the correctness of the alert signal.

According to another aspect of the invention, the device can also include a GPS unit, connected to the controller, for detecting the position of the device, thereby producing location data. Accordingly, the device provides the location data to the remote communication unit via the communication interface.

According to a further aspect of the invention, the communication interface generates a facsimile transmission and can also be connected to a printer.

According to another aspect of the invention, the communication interface consists of a wireless transceiver and the remote communication unit consists of a mobile transceiver.

The communication interface can transmit an audio message to the remote communication unit and the remote communication unit converts the audio message into sound.

The communication interface can also transmit a data message to the remote communication unit and the remote communication unit displays the data message.

The device can further include securing means for securing the device to the animal, such as a collar, an ear securing device, under the skin implant housing, and the like.

The device can further include an analog to digital converter, connected between the audio receiving device and the controller, wherein the analog to digital converter converts the audio signal into digital format, for the controller to collect, analyze and process.

The device can also include an amplifier, connected after the audio receiving device, for amplifying the audio signal.

The device can also include an audio-visual monitoring system for viewing an animal or a group of animals in distress and providing an attendant with alert signals.

In accordance with another aspect of the present invention, there is thus provided a method for identifying said sound patterns accompanying physiological processes and activities of an animal in general, and uttered by an animal in distress in particular, especially of a pregnant animal going into labor, for storing, analyzing and processing data related to said identified sound patterns and deviations therefrom, and for providing an attendant with respective alert signals and data, according to pre-programmed requirements, including the steps of receiving a sound signal, converting the sound signal into an audio signal, comparing the audio signal with animal pre-stored audio pattern, determining the decree of resemblance between the audio signal and the pre-stored audio pattern, thereby producing a likelihood value, storing the likelihood value, initiating an alert procedure when the likelihood value exceeds a pre-stored threshold value, and providing data according to pre-programmed requirements.

The following is a digital version of the method of the invention which includes the steps of:

receiving a sound signal, converting the sound signal into an audio signal, converting the audio signal into digital format, thereby producing a digital audio signal, comparing the digital audio signal with animal pre-stored audio pattern, determining the degree resemblance between the digital audio signal and the pre-stored audio pattern, thereby producing a likelihood value, storing the likelihood value, and initiating an alert procedure when the likelihood value exceeds a pre-stored threshold value, and providing data according to pre-programmed requirements.

The method can further include steps such as:

amplifying the audio signal before the step of comparing, filtering the audio signal after the step of receiving, filtering the digital audio signal before the step of comparing, enhancing portions of the digital audio signal before the step of comparing, and detecting the location coordinates of the animal and transmitting the location coordinates to the remote communication unit, when the likelihood value exceeds a pre-stored threshold value.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

The present invention overcomes the disadvantages of the prior art by providing a device which identifies sound patterns accompanying physiological processes and activities of an animal in general, and uttered by an animal in distress in particular, especially of a pregnant animal going into labor.

Figure 1:
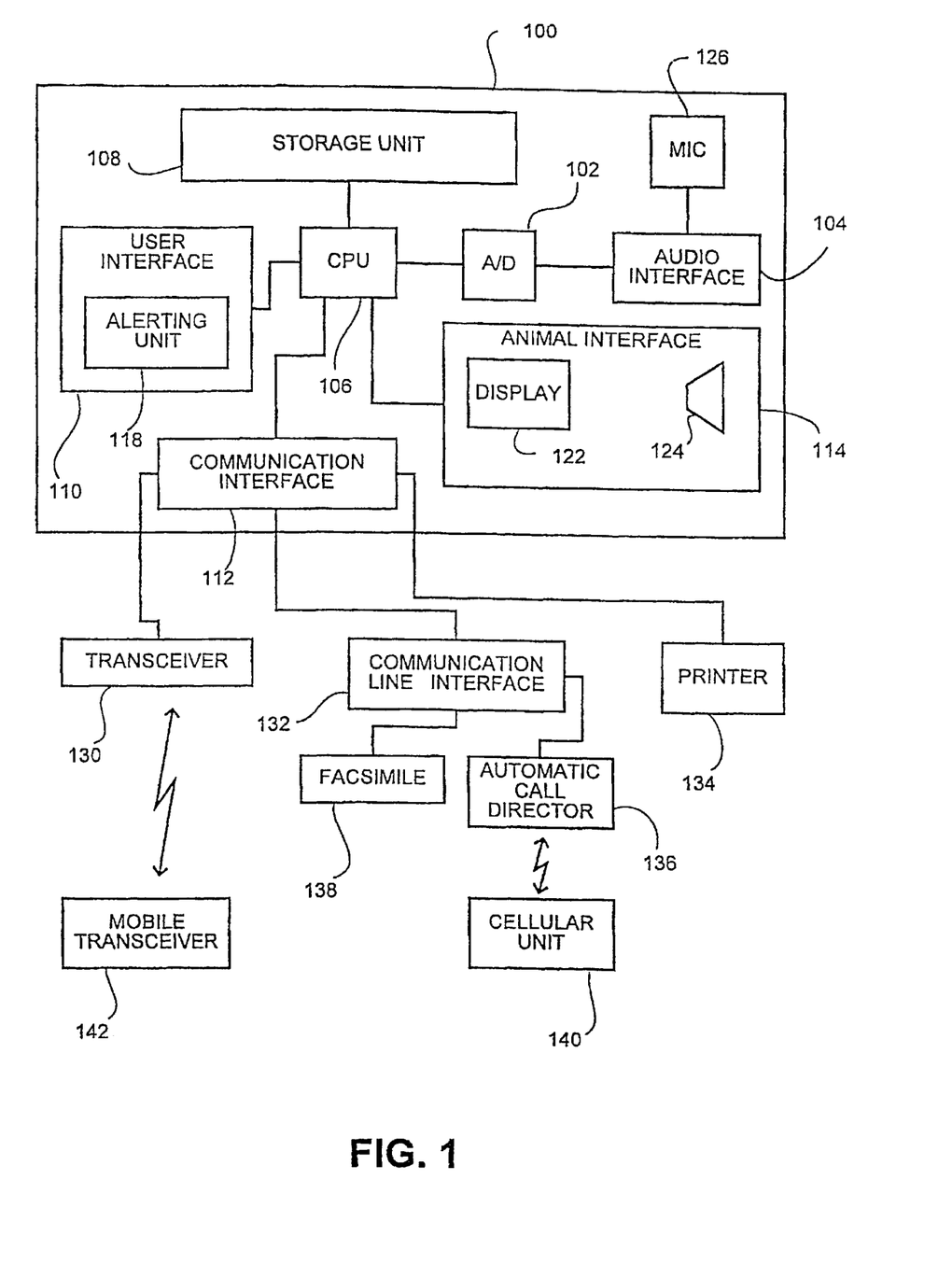
FIG. 1 is a schematic illustration of a device for detecting the delivery of a newborn animal, constructed and operative in accordance with a preferred embodiment of the present invention.

Reference is now made to FIG. 1, which is a schematic illustration of a device generally referenced 100, constructed and operative in accordance with a preferred embodiment of the present invention.

Device 100 includes a central processing unit (CPU) 106, an analog to digital (A/D) converter 102, an audio interface 104, a microphone 126, a communication interface 112, a user interface 110, an animal interface 114 and a storage unit 108.

CPU 106 is connected to the storage unit 108, the A/D converter 102, the animal interface 114, the communication interface 112 and the user interface 110.

The A/D converter 102 is further connected to the audio interface 104. The communication interface 112 is further connected to a plurality of communication devices such as a transceiver 130 for wireless communication, a printer 134 and a communication line interface 132 for connecting to a facsimile machine 138 and an automatic call director 136. The transceiver 130 is wirelessly linked to a mobile transceiver 142, which is carried by the attendant. The automatic call director 136 is capable of establishing a connection to any telephony destination, which in the present example is a cellular unit 140.

The animal interface 114 includes a display 122. The user interface 110 includes an alerting unit 118, for alerting an attendant which is not present in proximity to the animal in distress. It will be noted that the user interface 110 can also include a multimedia interface (not shown) for receiving instructions from a user, for example, pre-programming it to identify various kinds of animal sound patterns and to provide various data.

The audio interface 104 is basically an amplifier which can be connected to a sound sensitive detector such as the microphone 126. It will be noted that when the signal produced by the microphone is strong enough, then amplification is not necessary. Typically, this microphone 126 is placed in proximity to a delivering animal, or physically mounted thereon or implanted therein or in proximity to a group of animals. It will further be noted that microphone 126 can be a wireless microphone, wirelessly linked to the audio interface 104.

In the present example, both the A/D converter 102 and the audio interface 104 are implemented in a conventional PC sound card such as the sound-bluster, manufactured and produced by Creative Inc.

The storage unit 108, contains pre-stored sound patterns which were collected by recording a plurality of sound patterns accompanying physiological processes and activities of an animal in general, and uttered by an animal in distress in particular, especially of a pregnant animal going into labor. These sound patterns are used by the device 100, to determine whether a received sound can be regarded as a typical sound accompanying physiological processes and activities of an animal in or uttered by an animal in distress.

The audio interface 104 receives an audio signal from the microphone 126, amplifies it and provides the amplified analog audio signal to the A/D converter 102, which in turn digitizes it, thereby producing a digital audio signal. Then, the A/D converter 102 provides the digital audio signal to the CPU 106.

The CPU 106 accesses the storage unit 108, retrieves the pre-stored sound patterns and compares them to the digital audio signal, received from the A/D converter 102. As a result of the comparison, the CPU 106 produces a likelihood value L as a calculated value of the degree of resemblance between the digital audio signal and the best matching pre-stored sound pattern and stores said L value in the storage unit 108.

When the likelihood value L exceeds a pre-stored threshold P, then, the device executes an alerting procedure in which the alerting unit 118 is activated and the other external communication units are accessed via the communication interface 112 in a plurality of ways as follows:

The device 100 provides an alerting message to the transceiver 130 which in turn establishes a wireless communication link with the mobile transceiver 142, preferably carried by the attendant.

The device 100 provide an alerting message to the communication line interface 132, which in turn generates a facsimile transmission and transfers it to the facsimile machine 138. The facsimile machine can be located at a control room which goes into action when the attendant cannot be notified.

At the same time, the communication line interface provides a command to the automatic call directing unit 136, to initiate a call to a pre-stored telephony destination, which in the present example is a cellular unit 140, preferably carried by the attendant.

The device 100 provide an alerting print message to printer 134, which can be used as a log registry device. The user interface 110 may be used by the user to retrieve data according to pre-programmed requirements.

Figure 2:
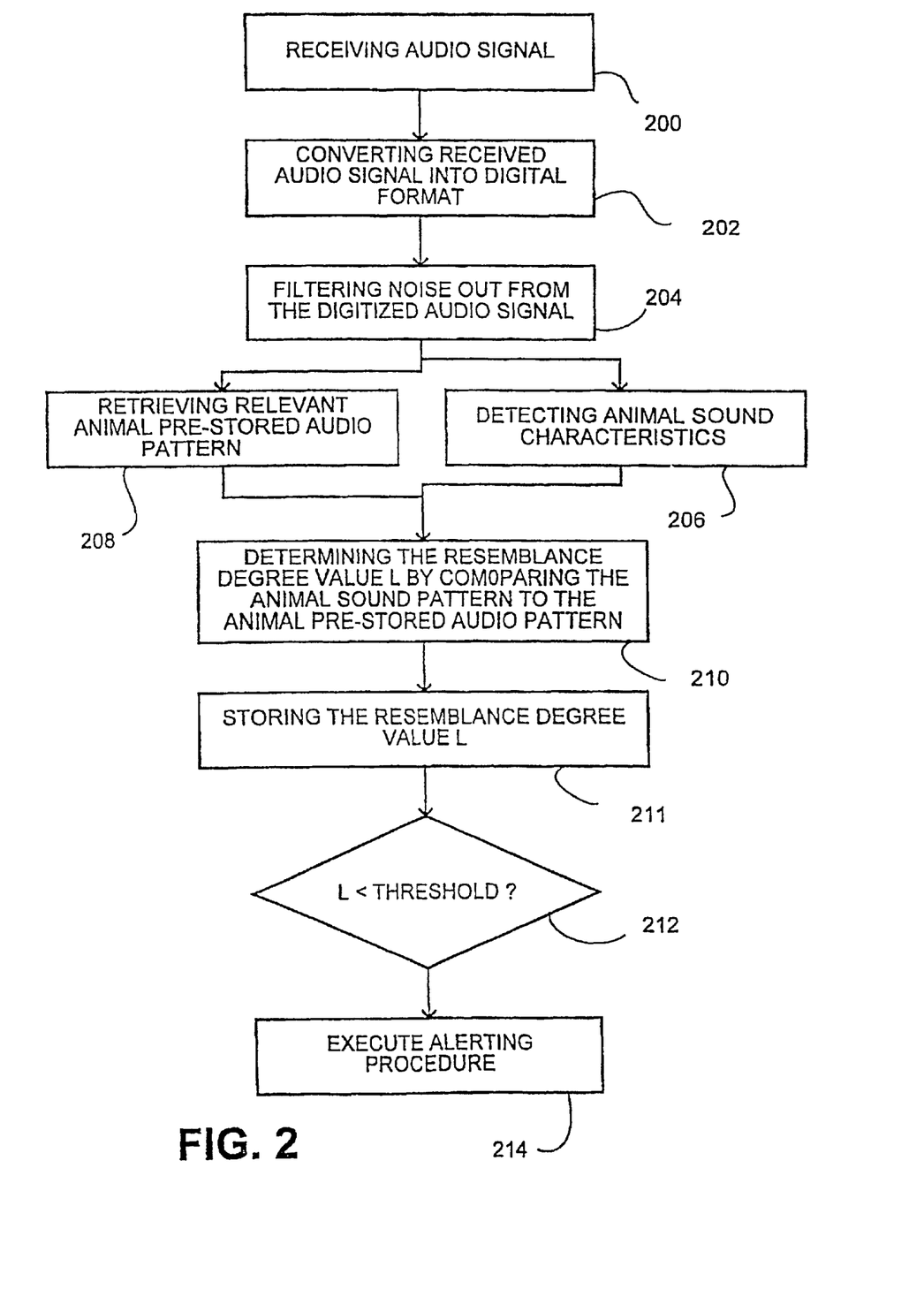
FIG. 2 is a schematic illustration of a method for operating the device of FIG. 1, operative in accordance with a preferred embodiment of the present invention.

Reference is now made to FIG. 2, which is a schematic illustration of a method for operating the device 100 of FIG. 1, operative in accordance with a preferred embodiment of the present invention.

In step 200, the device 100 receives a sound signal via the microphone 102, amplifies it and converts it into digital format (step 202).

In step 204, the CPU 204 processes the digital audio signal and prepares it for further analysis. The preparation consists of filtering procedures and enhancement procedures. The filtering procedures are used to filter out ambient noise and other undesired sounds. The enhancement procedure enhances portions of the digital audio signal, such as the voice of a delivering animal over the voices of nearby animals. At the end of step 206, the CPU 106 produces a digital signal which is a more focused version of the digital audio signal.

In step 206, the CPU 106 analyses the digital signal and identifies animal sound characteristics, such as frequencies, sound pattern, sound envelope, volume and the like.

In step 205, the CPU 106, accesses the storage unit 108 and retrieves the relevant animal pre-stored audio pattern. It will be noted that the storage unit 108 can store sound patterns which relate to various kinds of animals and animal species. Accordingly, for example, since sounds which are typical to a goat are of no relevance when the delivering animal is a cow, only cow related sound pattern is retrieved.

In step 210, the CPU 106 determines the degree of resemblance between the digital signal and the pre-stored audio pattern and produces a likelihood value L.

In step 211, the CPU 106 stores the likelihood value L in the storage unit 108.

In step 212, the CPU 106 detects if the likelihood value L exceeds a pre-stored threshold value which was selected to indicate when an attendant should be alerted. If so, then the CPU 106 initiates an alerting procedure, which can be selected from the above devices such as the alerting unit 118, the mobile transceiver 142, the printer 134 or any combination thereof.

It will be noted that each of the alerting messages can also include data which indicates the identifying device and the identified animal, when the device is attached thereto.

It will be appreciated that when dealing with a group of animals, it is also important to know the location of the identified animal in distress. In accordance with another aspect of the present invention, there is further provided a device which also detects and provides the location of the animal in distress.

Figure 3:
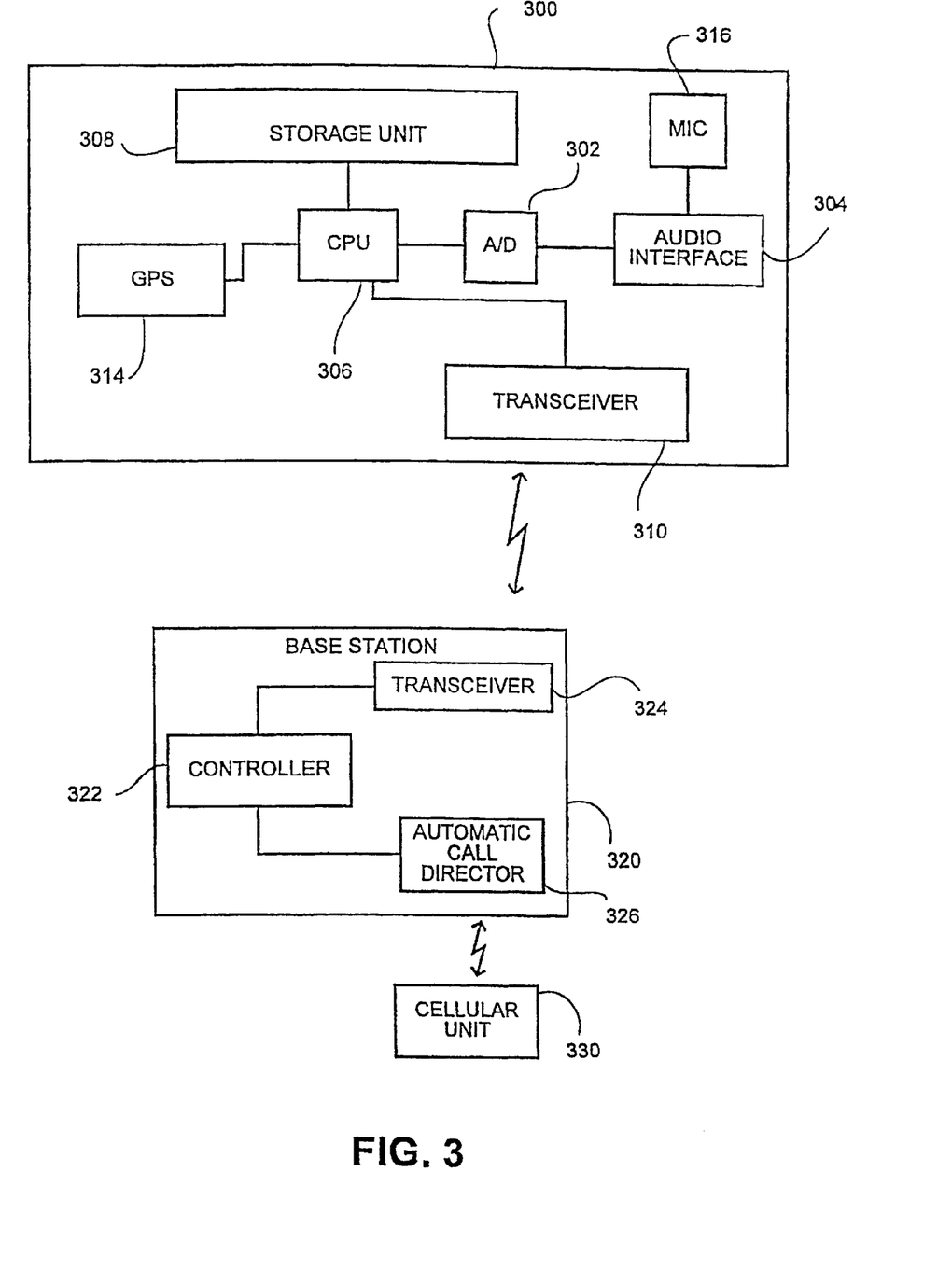
FIG. 3 is a schematic illustration of a device for detecting the delivery of a newborn animal, and a base station, both constructed and operative in accordance with another preferred embodiment of the present invention.

Reference is now made to FIG. 3, which is a schematic illustration of a device for identifying an animal in distress, generally referenced 300, and a base station, generally referenced 320, both constructed and operative in accordance with another preferred embodiment of the present invention.

Device 300 includes a CPU 306, an A/D converter 302, an audio interface 304, a microphone 316, a storage unit 108, a global positioning system (GPS) unit 314 and a wireless transceiver 310. The CPU 306 is connected to the A/D converter 302, the global positioning system (GPS) unit 314, the storage unit 108 and a wireless transceiver 310. The audio interface 304 is connected to A/D converter 302 and to the microphone 316.

The base station 320 includes a wireless transceiver 324, a controller 322 and an automatic call directing unit 326. The controller 322 is connected to the wireless transceiver 324 and to the automatic call directing unit 326.

The microphone 316 receives sounds, converts them into audio signal and provides the audio signal to the audio interface 304, which in turn amplifies it and provides the amplified signal to the A/D converter 302.

The A/D converter 302 converts the audio signal into digital format and provides the digitized signal to the CPU 306, which in turn, analyses and compares it with the pre-stored sound patterns stored in the storage unit 108.

When the CPU determines that the attendant has to be alerted, then it activates the GPS unit 314. The GPS unit 314 detects the actual position of the identifying device, and hence the approximate location of the animal in distress.

Then, the CPU 306 provides a message including the distress indication as well as the position data, to the base station via the transceiver 310.

The transceiver 324, at the base station 320, receives the message and provides it to the controller 322, which in turn activates the automatic call director 326. In the present example, the automatic call director 326 establishes a communication link with a cellular unit 330, preferably carried by the attendant.

It will be noted that the message received at the cellular unit 330, can include data, which is displayed on the screen of the mobile unit, or an audio alert, which describes the detected situation of the animal as well as verbal description of its position.

Figure 4:
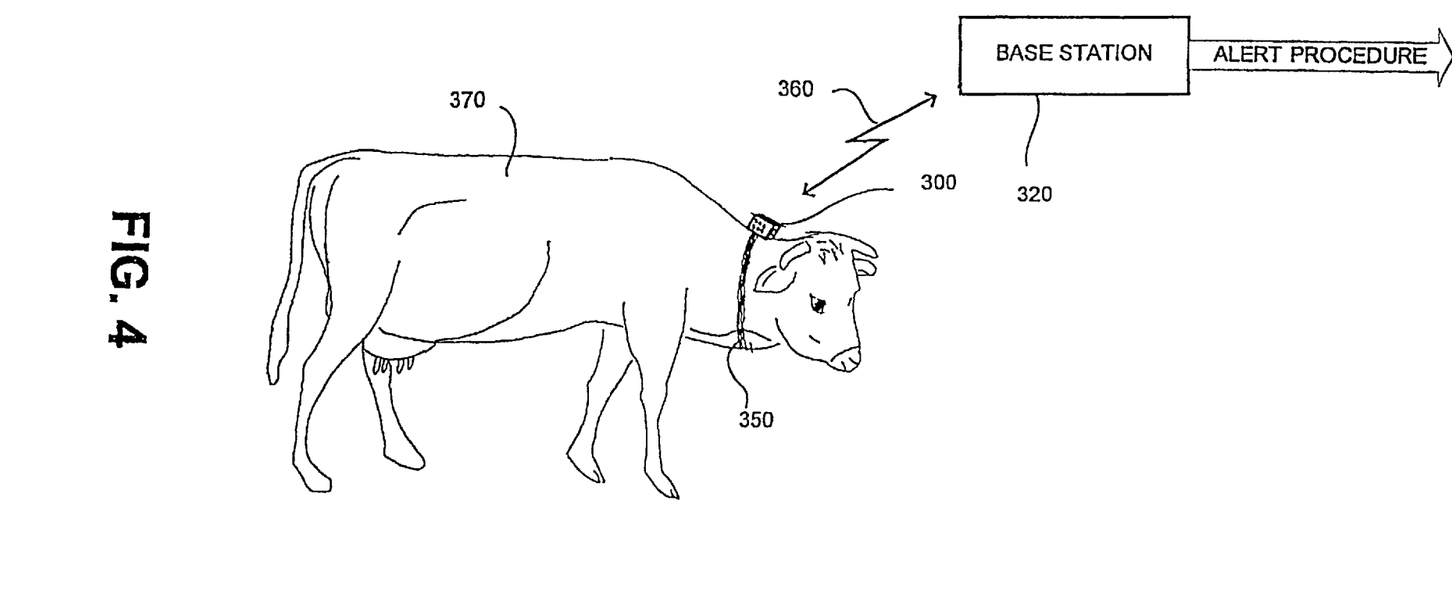
FIG. 4 is a schematic illustration of the device of FIG. 3, mounted on a cow.

Reference is now made to FIG. 4, which is a schematic illustration of the device of FIG. 3, mounted on a cow. Device 300 is secured to a cow 370 with a neck collar 350. The device 300 is linked to the base station 320, via a wireless link 360.

It will be noted that the device 300 can be secured to the animal in many ways, depending on the anatomy of the animal. For example, the device 300 can be secured to the ear or back of the animal. Furthermore, device 300 can be fit into an internal housing which is inserted under the skin of the animal.

Figure 5:
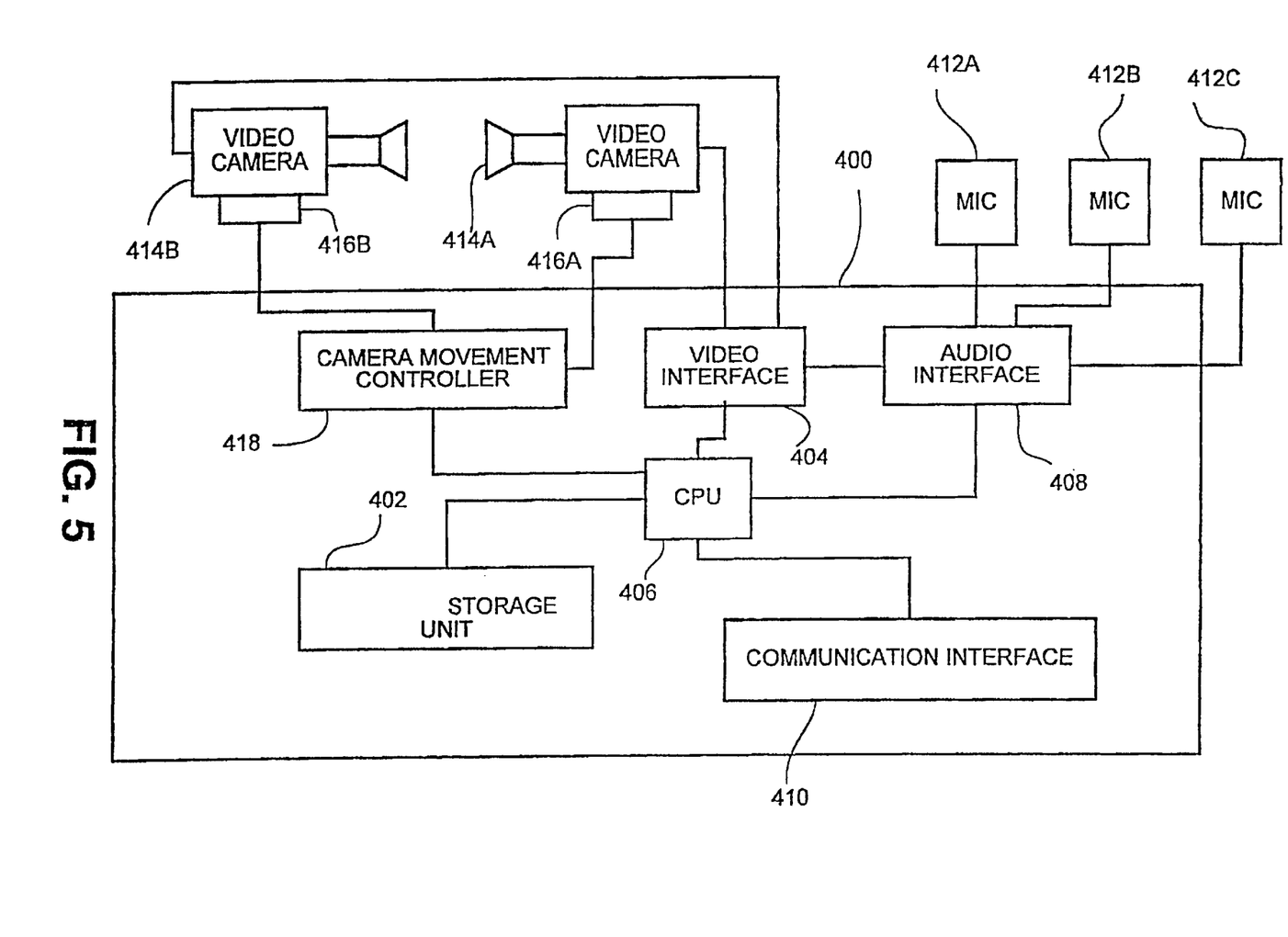
FIG. 5 is a schematic illustration of a system for monitoring the audio-visual condition of an animal or a group of animals in accordance with another embodiment of the present invention.

Reference is now made to FIG. 5, which is a schematic illustration of the system for monitoring the audio-visual condition of an animal or a group of animals, generally referenced 400, constructed and operative in accordance with another preferred embodiment of the present invention.

System 400 includes a CPU 406, a storage unit 402, a communication interface 410, an audio interface 408, a video interface 404 and a camera movement controller 418.

The CPU 406 is connected to the storage unit 402, the communication interface 410, the audio interface 408, the video interface 404 and the camera movement controller 418.

System 400 is generally located in proximity to an animal or a group of animals and monitors the sounds which they produce by utilizing a plurality of microphones 412A, 412B and 412C, all of which are connected to and controlled by the audio interface 408.

System 400 also monitors the movements and general behavior of the animals by utilizing a plurality of video cameras 414A and 414B, all connected to the video interface 404.

In the present example, each of the cameras 414A and 414B is mounted on a motorized basis, 416A and 416B, respectively, which is operable to point its associated camera to various directions. Each motorized basis, 416A and 416B, is connected to and controlled by the camera movement controller 418.

Each of the video cameras 414A and 414B provides video signals to the video interface 404. The video interface 404 can store or record the video signals. The video interface 404 can also control some optical properties of the cameras such as focal length, zoom angle, aperture setting, shutter speed and the like. It will be noted that these properties can also be controlled automatically by the camera.

Each of the microphones converts received sounds into an audio signal and provides this audio signal to the audio interface 408. The audio interface 408, converts the audio signals into respective digital audio signals and provides them to the CPU 406. The CPU 404 analyzes digital audio signals and compares their patterns with audio patterns which were pre-stored in storage unit 402. When a reliable match is detected, then the CPU 406 provides a command to the communication interface to connect to a pre-stored remote address, which can be a telephone line, an IP address, a cellular unit and the like.

The supervisor which is located at that remote address, communicates with the system 400, thereby receiving information related to the identified pattern, the time of identification, the identity of the receiving microphone through which the identified pattern was received and the like.

The supervisor can also receive a video signal which is detected by either of cameras 414A and 414B. If desired, the supervisor can provide system 400 with a command to direct the cameras to various directions. Such a command is received in the CPU 406, via the communication interface 410. Then, the CPU 406 provides this command to the camera movement controller 418, which in turn provides it to the respective camera.

It will be noted that system 400 can also initiate a camera movement automatically. In this case, when a received digital audio signal is found to be matching a pre-stored sound pattern, then the CPU 406 determines the location of the receiving microphone, produces a camera movement command and provides it to the camera movement controller 418, which in turn activates the respective motorized basis.

It will be appreciated by persons skilled in the art that the present invention is not limited to what has been particularly shown and described hereinabove. Rather the scope of the present invention is defined only by the claims which follow.

What is claimed is:

1. An apparatus for automatically identifying when an animal is in distress based upon animal sound patterns produced in distress, said apparatus comprising:

an audio receiving device in, or proximate to, a selected animal for receiving a sound pattern produced in proximity to the selected animal and for converting the received sound pattern into an audio signal;

a securing member for securing said device in or to the selected animal;

a controller connected to said device;

a storage unit connected to said controller for storing a plurality of pre-stored audio patterns, each of said pre-stored audio patterns corresponding to a respective sound expected to be produced by an animal of the same type as the selected animal when in a respective different type of distress; and a communication interface connected to said controller for communicating with a remote communication unit located in proximity to an attendant, wherein said controller receives said audio signal from said device and compares said audio signal with said pre-stored audio patterns to determine which of said pre-stored audio patterns best matches said audio signal, wherein said controller produces a likelihood value representing a respective degree of resemblance between said audio signal and the best-matching pre-stored audio pattern, wherein said controller compares said likelihood value with a pre-stored threshold, and wherein said controller automatically communicates a command to said communication interface when the likelihood value exceeds a pre-stored value, said communication interface automatically communicating a signal to the remote communication unit in response to said command informing the remote communication unit of the respective distress corresponding to the best-matching pre-stored audio pattern.

2. The apparatus of claim 1, wherein said pre-stored audio patterns correspond to respective types of distress related to at least one of cardiac, respiratory, digestive, ruminative and reproductive processes.

3. The apparatus of claim 1, wherein said storage unit stores pre-stored audio patterns for each of a plurality of types of animals, wherein said controller compares said audio signal only with those of said pre-stored audio patterns corresponding to the type of the selected animal.

4. The apparatus of claim 1, wherein the command indicates the identity of the selected animal from among a plurality of animals.

5. The apparatus of claim 1, further comprising a user interface connected to said controller for receiving programming instructions from a user.

6. The apparatus of claim 1, further comprising an animal interface connected to said controller for maintaining an open communication line to the remote communication unit located in proximity to the attendant, said animal interface receiving the sound patterns generated in proximity to the selected animal, whereby the attendant can listen to the generated sound patterns and confirm the correctness of a command received via said communication interface.

7. The apparatus of claim 1, further comprising a GPS unit connected to said controller for detecting a position of said device and for producing location data based upon the detected position, wherein said device provides said location data to said remote communication unit via said communication interface.

8. The apparatus of claim 1, wherein said communication interface generates a facsimile transmission.

9. The apparatus of claim 1, wherein said communication interface is further connected to a printer.

10. The apparatus of claim 1, wherein said communication interface includes a wireless transceiver for communicating signals with a mobile transceiver included in the remote communication unit.

11. The apparatus of claim 1, wherein said communication interface transmits an audio message to the remote communication unit to be converted into sound at the remote communication unit.

12. The apparatus of claim 1, wherein said communication interface transmits a data message to the remote communication unit to be displayed at the remote communication unit.

13. The apparatus of claim 1, wherein said securing member is selected from the group consisting of:

a collar;

a back securing assembly;

an ear securing device; and an internal housing.

14. The apparatus of claim 1, further comprising an analog to digital converter connected between said audio receiving device and said controller, said analog to digital converter converting said audio signal into digital format for said controller to process.

15. The apparatus of claim 1, further comprising an amplifier connected after said audio receiving device for amplifying said audio signal.

16. The apparatus of claim 1, further comprising:

a video interface connected to said controller; and at least one video camera, connected to said video interface, for detecting movement of the selected animal.

17. The apparatus of claim 16, further comprising:

a camera movement controller; and at least one motorized basis, connected to said camera movement controller, wherein at least a selected one of said at least one video camera is mounted on a selected one of said at least one motorized basis, wherein the selected motorized basis directs the selected video camera.

18. An system for automatically identifying when an animal is in distress based upon animal sound patterns produced in distress, said system comprising:

an apparatus in, or proximate to, a selected animal; and a remote communication unit located in proximity to an attendant, wherein said apparatus comprises:

an audio receiving device in, or proximate to, the selected animal for receiving a sound pattern produced in proximity to the selected animal and for converting the received sound pattern into an audio signal;

a securing member for securing said device in or to the selected animal;

a controller connected to said device;

a storage unit connected to said controller for storing a plurality of pre-stored audio patterns, each of said pre-stored audio patterns corresponding to a respective sound expected to be produced by an animal of the same type as the selected animal when in a respective different type of distress; and a communication interface connected to said controller for communicating with said remote communication unit located in proximity to the attendant, wherein said controller receives said audio signal from said device and compares said audio signal with said pre-stored audio patterns to determine which of said pre-stored audio patterns best matches said audio signal, wherein said controller produces a likelihood value representing a respective degree of resemblance between said audio signal and the best-matching pre-stored audio pattern, wherein said controller compares said likelihood value with a pre-stored threshold, and wherein said controller automatically communicates a command to said communication interface when the likelihood value exceeds a pre-stored value, said communication interface automatically communicating a signal to said remote communication unit in response to said command informing said remote communication unit of the respective distress corresponding to the best-matching pre-stored audio pattern.

19. The system of claim 18, wherein said pre-stored audio patterns correspond to respective types of distress related to at least one of cardiac, respiratory, digestive, ruminative and reproductive processes.

20. The system of claim 18, wherein said storage unit stores pre-stored audio patterns for each of a plurality of types of animals, wherein said controller compares said audio signal only with those of said pre-stored audio patterns corresponding to the type of the selected animal.

21. A method for automatically identifying when an animal is in distress based upon animal sound patterns produced in distress, said method comprising the steps of:

securing an audio receiving device in, or proximate to, a selected animal for receiving a sound pattern produced in proximity to the selected animal;

initially storing a plurality of pre-stored audio patterns, each of the pre-stored audio patterns corresponding to a respective sound expected to be produced by an animal of the same type as the selected animal when in a respective different type of distress;

converting a sound pattern received by the device into an audio signal;

comparing the audio signal with the pre-stored audio patterns to determine which of the pre-stored audio patterns best matches the audio signal;

producing a likelihood value representing a respective degree of resemblance between the audio signal and the best-matching pre-stored audio pattern;

comparing the likelihood value with a pre-stored threshold; and automatically communicating a signal to a remote communication unit located in proximity to an attendant when the likelihood value exceeds a pre-stored value, the signal informing the remote communication unit of the respective distress corresponding to the best-matching pre-stored audio pattern.

22. The method of claim 21, wherein the pre-stored audio patterns correspond to respective types of distress related to at least one of cardiac, respiratory, digestive, ruminative and reproductive processes.

23. The method of claim 21, wherein said storing step stores pre-stored audio patterns for each of a plurality of types of animals, and wherein the first-mentioned comparing step compares the audio signal only with those of the pre-stored audio patterns corresponding to the type of the selected animal.

* * * * *